United States Patent [19]
Bergersen

[11] Patent Number: 4,919,612
[45] Date of Patent: Apr. 24, 1990

[54] DENTAL-FORM EXPANSION APPLIANCE

[76] Inventor: Earl O. Bergersen, 950 Green Bay Rd., Winnetka, Ill. 60093

[21] Appl. No.: 117,565

[22] Filed: Nov. 6, 1987

[51] Int. Cl.⁵ .............................................. A61C 7/00
[52] U.S. Cl. ........................................ 433/6; 433/24
[58] Field of Search ......................................... 433/5, 6

[56] References Cited

U.S. PATENT DOCUMENTS 4,505,673  3/1985  Yoshii .................................... 433/6

FOREIGN PATENT DOCUMENTS 2749802  11/1978  Fed. Rep. of Germany .......... 433/6

Primary Examiner—Robert Peshock
Attorney, Agent, or Firm—Hill, Van Santen, Steadman & Simpson

[57] ABSTRACT

An orthodontic appliance is provided which has upper and lower tooth receiving troughs which include sockets for the canines and posterior teeth, the sockets being laterally spaced at a distance greater than the normal lateral spacing of the patient's posterior teeth, and a mesio-distal dimension of the canine sockets is greater than the normal mesio-distal dimension of the patient's canines to provide expansion in a deciduous or mixed dentition.

13 Claims, 1 Drawing Sheet

DENTAL-FORM EXPANSION APPLIANCE

BACKGROUND OF THE INVENTION

1. Field of the Invention

The invention relates to tooth positioning appliances, and in particular to an appliance to be used with deciduous dentition or mixed dentition to expand the posterior segments.

2. Description of the Prior Art

Over crowding of the teeth, particularly the anterior teeth is one condition which can be corrected with orthodontic treatment. Oftentimes metallic bands and wires are used in the permanent dentition stage to provide the desired spacing. There have also been provided devices such as my prior device disclosed in U.S. Pat. No. 4,139,944 in which a plastic removable positioner is provided for use in correcting certain conditions in a permanent or mixed dentition stage.

SUMMARY OF THE INVENTION

The present invention provides a U-shaped appliance which may be used for the upper and lower arches with a connecting isthmus or plate that engages the occlussal surfaces of the teeth. The appliance can be used for either deciduous teeth only or can be used for mixed dentition. The mixed dentition would consist of permanent upper and lower incisors (central and lateral incisors) and first permanent molars, deciduous canines, decidious first molars and deciduous second molars. The set-up of the incisors would be quite upright especially in the lower arch (about 85° to the mandibular plane or a 130° interincisal angle) to prevent labial tipping of the lower incisors with expansion of the canines and molars. The lateral spacing of the inter-canine, first deciduous molar-to-molar and the second deciduous molar-to-molar would be expanded for example by about 7 mm from their normal position and the mesial-distal canine-to-canine distance would be increased for example by about 4 mm from its normal distance.

Individual sockets are provided in the appliance for the posterior teeth and because of the early stage of development of the patient's mouth at the age up to mixed dentition, the posterior teeth will move to the expanded position of the preformed appliance to provide increased spacing for the incisors.

DESCRIPTION OF THE PREFERRED EMBODIMENTS

Figure 1:
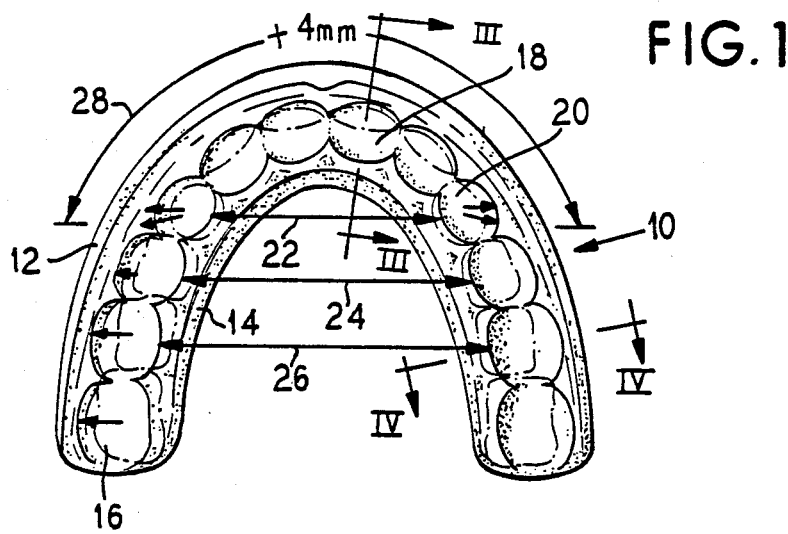
FIG. 1 is an occlussal view of an appliance embodying the principles of the present invention.
Figure 2:
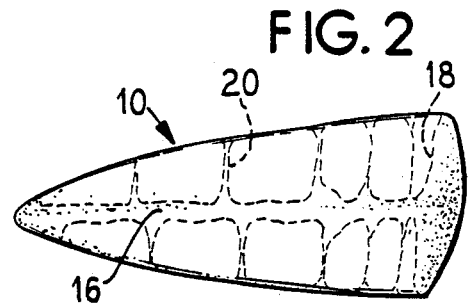
FIG. 2 is a buccal elevational view of the appliance of FIG. 1.
Figure 3:
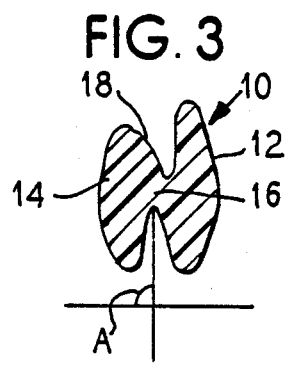
FIG. 3 is a sectional view taken generally along the line III—III of FIG. 1.
Figure 4:
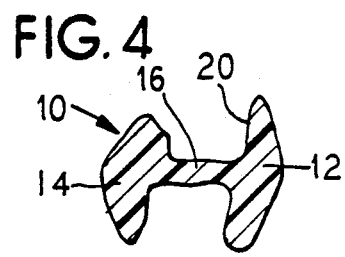
FIG. 4 is a sectional view taken generally along the line IV—IV of FIG. 1.

In FIG. 1 there is a shown an appliance 10 embodying the principles of the present invention in an occlussal or plan view. The appliance 10 is U-shaped for the upper and lower arches of a human mouth. The appliance has an outer labial-buccal flange 12 and an inner lingual flange 14, the flanges 12, 14 extending superior to and inferior to a connecting isthmus or plate 16 that engages the occlussal surfaces of the teeth in an appliance for expanding both upper and lower arches. The appliance could also be provided for use with only an upper or lower arch, and in such cases, the flanges would extend only superiorly or inferiorly, respectively.

Three different types of appliances can be provided, one for use with only deciduous teeth present, one for use with mixed dentition and one for use with permanent dentition. The mixed dentition stage would consist of permanent upper and lower incisors (central and lateral incisors) and first permanent molars, deciduous canines, deciduous first molars and deciduous second molars.

The area between the flanges 12, 14 is in the form of a generally continuous groove 18 in the incisor area and individual sockets or depressions 20 are provided for the canines, first deciduous molars and second deciduous molars.

The groove 18 for the incisors is formed quite upright, especially in the lower arch, to result in an angle A between the incisor and the mandibular plane of approximately 85° to prevent labial tipping of the lower incisors with expansion of the canines and molars.

The appliance is formed so that an inter-canine spacing 22, a first deciduous molar-to-molar spacing 24 and a second deciduous molar-to-molar spacing 26 are expanded by a desired amount which may be on the order of approximately 1-20 mm from their normal position to cause the teeth in those positions to expand buccally. The sockets 20 for the canines and posterior teeth are also moved posteriorly from a normal position so that a mesial distal distance 28 from canine-to-canine is increased by a desired amount which may be on the order of about 1-15 mm from a normal size. Thus, the posterior teeth from the canines back are moved distally as well as buccally to provide increased spacing for the incisors.

FIG. 1 illustrates the normal teeth position in phantom where it is seen that the sockets from the canines rearwardly are positioned distally and buccally from the normal teeth positions.

Figure 5:
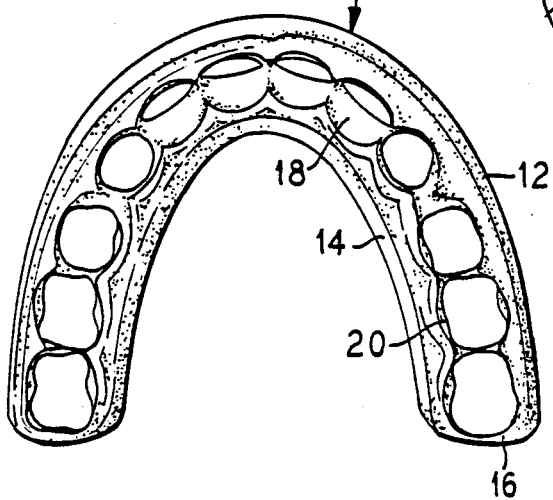
FIG. 5 is an occlussal view of the device showing the dentition after treatment with the device.

FIG. 5 illustrates the condition of the teeth after a sufficient length of treatment with the appliance 10 in which the posterior teeth have expanded out to be seated in the sockets of the appliance.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

I claim in my invention:

1. An orthodontic appliance of the type which is generally U-shaped in plan view and which includes a tooth receiving trough for at least one of the upper or lower row of a patient's teeth, said trough being formed between a labial-buccal flange and a lingual flange, said appliance being preformed with individual tooth receiving sockets for each of the canine and posterior teeth and said sockets being positioned with a lateral spacing in excess of the normal lateral tooth spacing of the patient.

2. An orthodontic appliance according to claim 1, wherein said lateral spacing of said sockets is in the range of 1-20 mm greater than the normal tooth spacing.

3. An orthodontic appliance according to claim 1, wherein a mesio-distal spacing from one canine socket to the other canine socket is greater than the normal mesio-distal dimension of the patient from one canine to the other canine.

4. An orthodontic appliance according to claim 3, wherein the mesio-distal spacing of the canine sockets is in the range of 1-15 mm greater than the normal canine mesio-distal dimension.

5. An orthdontic appliance according to claim 1, including both upper and lower troughs.

6. An orthodontic appliance for expansion of at least one of the upper or lower arches in the early dentition stage of a patient comprising:
   a generally U-shaped appliance including a tooth receiving trough for at least one of the upper or lower row of a patient's teeth,
   said appliance being preformed with individual tooth receiving sockets for each of the canine and posterior teeth,
   said sockets having a mesio-distal spacing from one canine socket to the other canine socket greater than the normal canine mesio-distal dimension of the patient.

7. An orthodontic appliance according to claim 6, wherein the mesio-distal spacing of the canine sockets is in the range of 1-15 mm greater than the normal canine mesio-distal dimension.

8. An orthodontic appliance according to claim 6, wherein a lateral spacing of said sockets is in excess of the normal lateral tooth spacing of the patient.

9. An orthodontic appliance according to claim 8, wherein said lateral spacing of said sockets is in the range of 1-20 mm greater than the normal tooth spacing.

10. An orthodontic appliance according to claim 6, including both upper and lower troughs.

11. A method of positioning teeth comprising the steps of:
    providing an orthodontic positioner of the type which is generally U-shaped in plan view and includes in at least one of the top or bottom thereof a tooth receiving trough for receiving and positioning teeth, said providing step comprising selecting a positioner having in the trough or troughs therein depressions for the patient's incisor teeth and individual depressions for the patient's posterior teeth, said depressions for the incisor teeth being sized for the normal spacings of the incisors and said depressions for the posterior teeth being laterally spaced at a distance greater than the normal lateral spacing of the posterior teeth of the patient, applying the positioner for use by a patient during at least one of a deciduous, mixed or permanent dentition stage of development, whereby such use causes the posterior teeth to expand at least one of buccally or distally 12. The method of claim 11, wherein said providing step includes providing a positioner having tooth receiving troughs in both the top and bottom thereof.

13. The method of claim 11, wherein said providing step includes providing a positioner wherein the mesio-distal spacing of the depressions for receiving the canines is greater than the mesio-distal spacing of the patient's canines.

* * * * *